United States Patent [19]

Failla et al.

[11] Patent Number: 4,480,641
[45] Date of Patent: Nov. 6, 1984

[54] TIP CONFIGURATION FOR A LIGATING CLIP APPLIER

[75] Inventors: Stephen J. Failla, Chester; Joseph D'Innocenzio, Kenilworth, both of N.J.

[73] Assignee: Ethicon, Inc., Somerville, N.J.

[21] Appl. No.: 345,974

[22] Filed: Feb. 5, 1982

[51] Int. Cl.³ .......................... A61B 17/12; B21D 9/08
[52] U.S. Cl. .............................. 128/326; 227/DIG. 1; 72/410
[58] Field of Search ............... 128/325, 326, 321, 346; 72/410; 227/DIG. 1 B

[56] References Cited

U.S. PATENT DOCUMENTS

| | | | |
|---|---|---|---|
| 2,618,268 | 11/1952 | English | 128/321 |
| 2,774,268 | 12/1956 | Kagan | 72/410 |
| 3,270,745 | 9/1966 | Wood | 128/325 |
| 3,680,352 | 8/1972 | Wunder | 72/410 |
| 3,906,957 | 9/1975 | Weston | 128/321 |
| 4,430,997 | 2/1984 | DiGiovanni et al. | 128/326 |

FOREIGN PATENT DOCUMENTS 2088723  6/1982  United Kingdom ............... 128/325

Primary Examiner—C. Fred Rosenbaum
Assistant Examiner—Gene B. Kartchner
Attorney, Agent, or Firm—Donal B. Tobin

[57] ABSTRACT

A multiple clip applier including a handle and a cartridge which holds a large number of ligating clips and which snaps into a cartridge-receiving channel on the handle. The handle operates like an elongated scissors with scissors handles at one end and jaws at the other to which clips may be delivered in rapid succession. Opening and closing the scissors handles operates the mechanism of the handle to open and close the jaws and to provide a long stroke motion for delivering clips from the end of the cartridge to the nose section. Clips may be indexed through the cartridge by reciprocating parts of the cartridge with respect to one another with a short stroke cocking motion captured from the long stroke delivery motion from a cooperating slot and pin mechanism. These two motions are accomplished within the envelope of motion of the normal opening and closing of the scissors handles to operate the jaws of the applier and to feed and index clips from the cartridge to the nose. The mechanism of the present invention permits the overall shape of the handle to be small, compact and readily adaptable for use even deep in an incision site.

3 Claims, 16 Drawing Figures

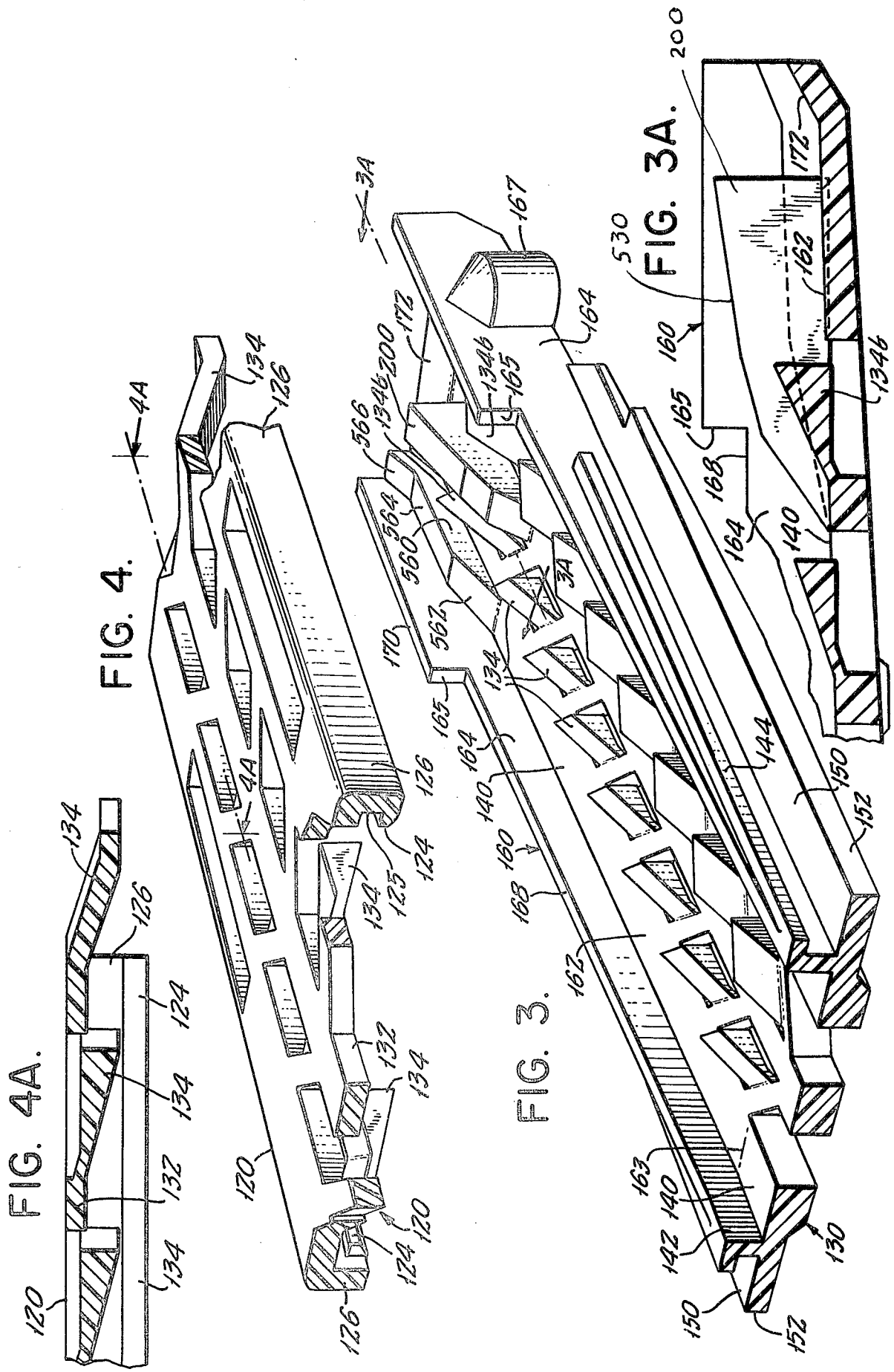

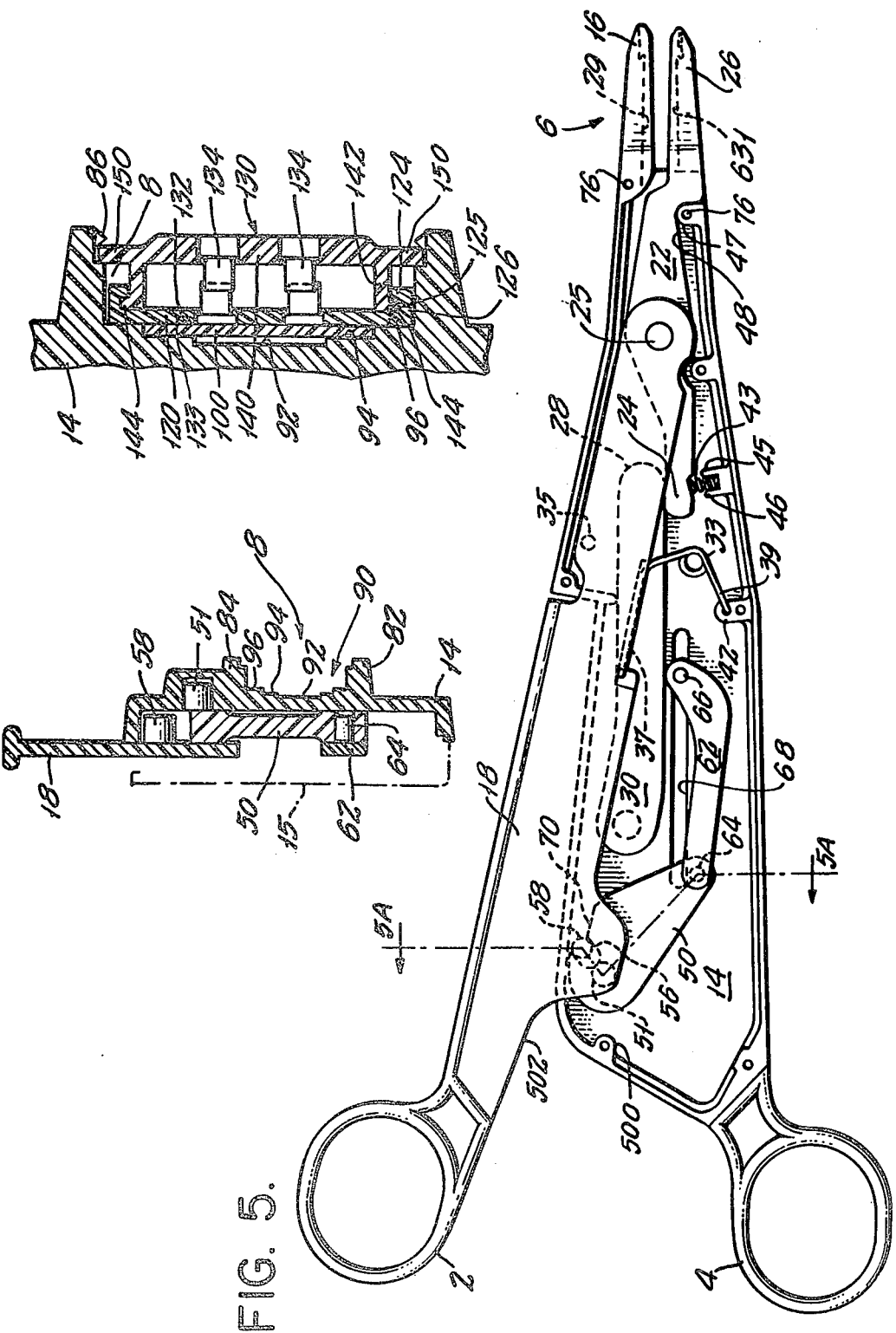

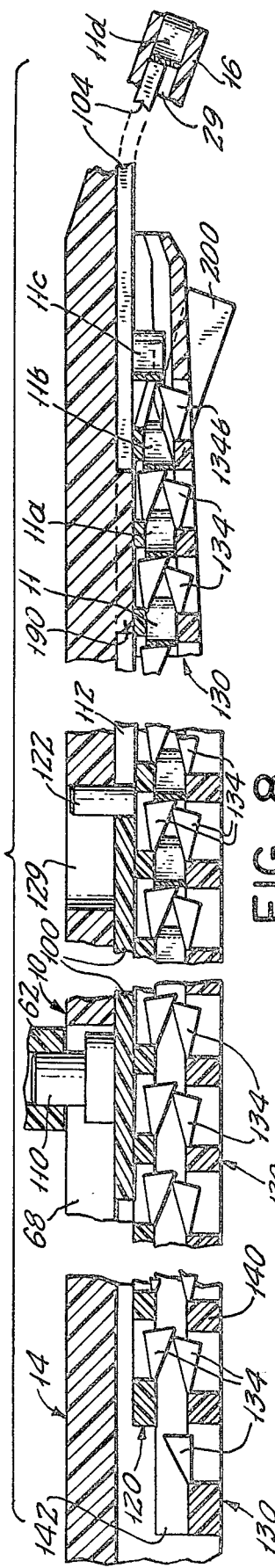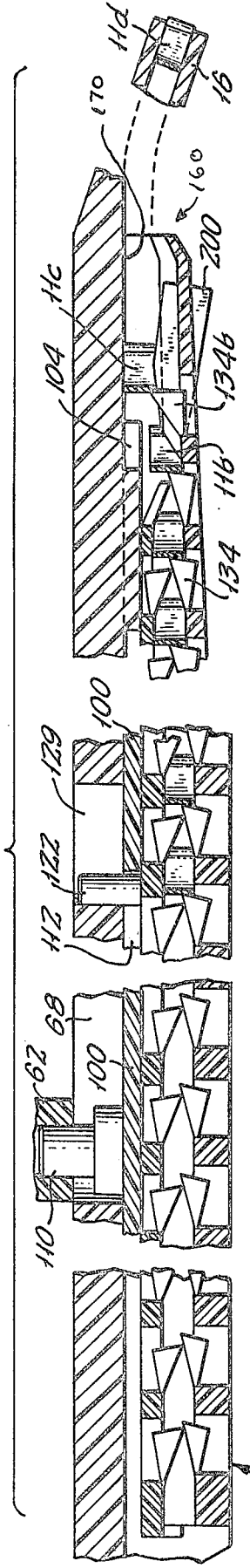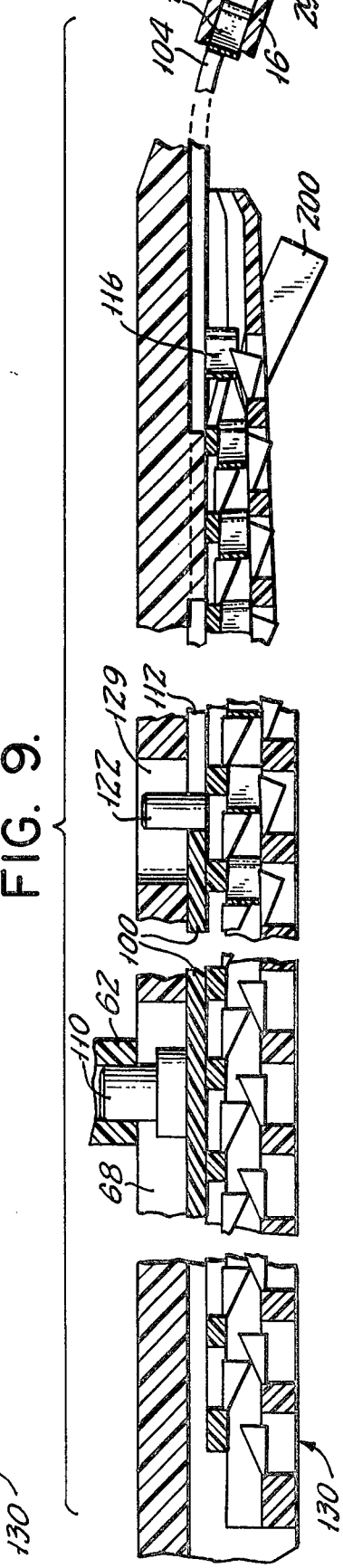

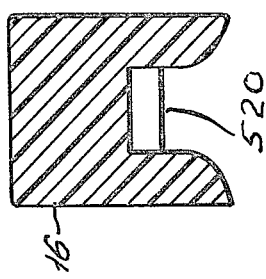
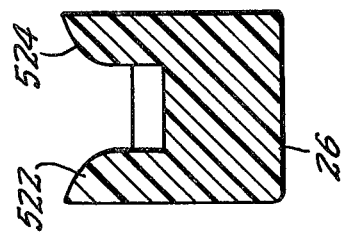
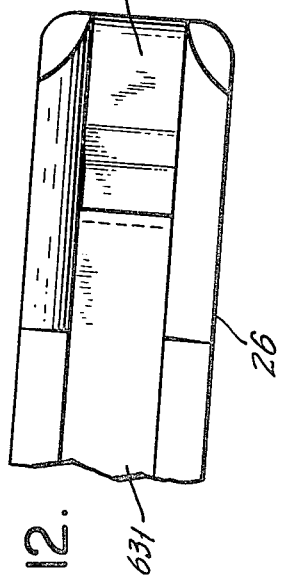
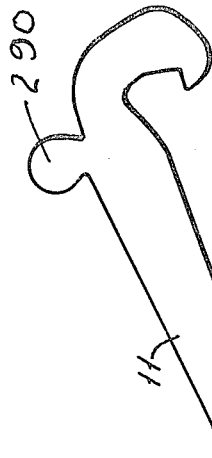
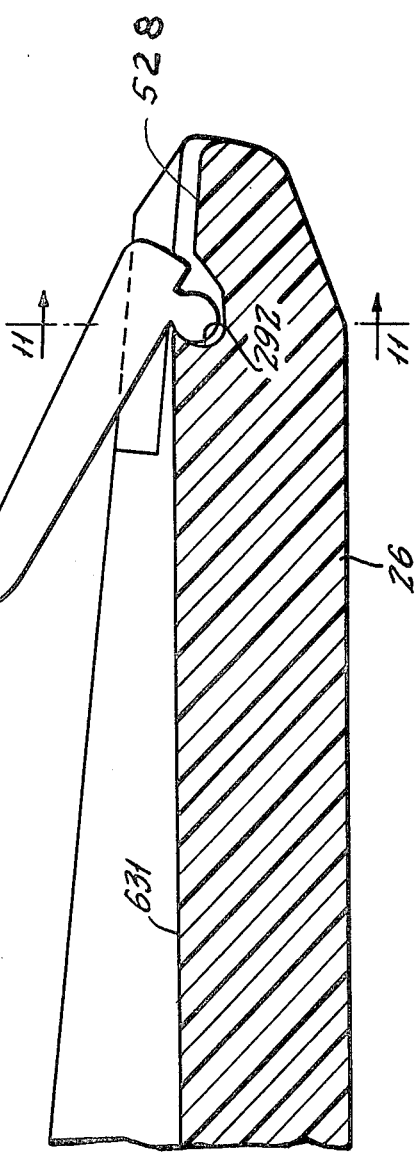

TIP CONFIGURATION FOR A LIGATING CLIP APPLIER

BACKGROUND OF THE INVENTION

The present invention relates to an apparatus for applying surgical clamps and clips and more particularly to the configuration of the jaw tips of a multiple clip applier.

A separate application Ser. No. 345,973, filed the same day as the application and assigned to the same assignee as this application, is directed to the handle portion of the Multiple Clip Applier. Another separate application Ser. No. 346,976, filed the same day as this application and assigned to the same assignee as this application, is directed to the cartridge portion of the Multiple Clip Applier.

In the past, when surgeons wished to cut a blood vessel, they would commonly suture it in two places spaced a short distance along the vessel and then cut between the sutures. Even for a skilled surgeon, the manipulations required to place two sutures about a vessel and then tie and cut the sutures can be time consuming. In recent years, the practice of using metal or plastic clips to ligate a vessel has gained increasing acceptance. Instead of suturing a vessel in two places, a surgeon need only apply two clips to the vessel and then cut between the clips. In many instances, the clips are applied one at a time as shown, for example, in U.S. Pat. No. 3,713,533. A clip is removed from a clip holder, loaded into the jaws of a clip applier and then the loaded applier is inserted into the ligation site and the clip is applied. Although this provides a perfectly satisfactory ligating technique, it can be slow because time is required to load the individual clips and to transfer them into the operating site for application.

Attempts have been made to provide a multiple clip applier where the applier itself supports a cartridge of many clips. The devices showing in U.S. Pat. No. 2,874,384 employs a multiple clip cartridge placed on the end of an auxiliary arm attached to the pivot point of an ordinary hemostat. Although such devices may provide satisfactory results, the user is required to place two fingers in the ring holes and close the hemostat about a vessel to be ligated. The auxiliary arm is then operated by a third finger while the hemostat is still held by the user. The applier must be rotated into position and compressed to set a clip about the vessel. This is a difficult and slow motion which many surgeons may find uncomfortable to use.

In the multiple stapler shown U.S. Pat. No. 3,082,426, one must close the rings of the scissors type hemostat part way to hold the vessel. One must then slide a staple advance mechanism forward with ones index finger while holding the rings of the hemostat with one's thumb and third finger until the staple advances into the hemostat jaws and surrounds the vessel. The user then continues to close the hemostat jaws to set the staple about the vessel.

The multiple clamp appliers shown in U.S. Pat. No. 2,968,041 use a pistol-grip action where clips are applied by jaws at the end of a long barrelled instrument operated by a pistol-grip handle at the other end of the instrument. Other devices have used a syringe-type action where the user pushes a plunger with his thumb through a barrel on the end of which is supported an anvil for collapsing the staple about the vessel. See, for example, U.S. Pat. No. 3,079,608.

Still other units use a pump action motion where the vessel is held in the jaws of a hemostat and the staple is advanced and set about the vessel by sliding a staple cartridge along the hemostat body. See, for example, U.S. Pat. No. 3,592,377.

It is desirable to have a multiple clip applier that may be operated with one hand using the familiar scissors action of a hemostat. The total envelope of the scissors motion should be small so that the instrument may be comfortably operated without using unusual manipulations. The small envelope of motion permits the instrument to be used in the confined space of a surgical incision. The normal scissors action of a hemostat provides good motor control for the surgeon while he is placing the clip about the vessel to be ligated and while he is closing the clip to seal off the vessel. It is desirable to have a large magazine of clips so that the surgeon does not have to change cartridges during an operation. There should be enough clips to permit the surgeon to discharge a few clips at the beginning of the operation to make sure that he is using with the correct type and size of clip. It is desirable to avoid motions which require the surgeon to use both hands to apply a clip or which require awkward manipulation of some of the fingers while other fingers are holding a ring-type instrument. Such manipulations may tire the surgeon and also extend the operating time. It is also desirable to have an instrument which may be inexpensively manufactured so that the entire device could be disposable to eliminate the expense of cleaning and sterilizing an instrument and to avoid the hazard of cross-infection from an improperly sterilized instrument.

SUMMARY OF THE INVENTION

The present invention provides a multiple clip applier with a large cartridge of clips removably affixed to a scissors-type handle. The handle body houses a mechanism for feeding clips from the cartridge to the jaws of the applier, for indexing clips through the cartridge and for setting the clips about the vessel to be ligated. The handle mechanism is driven by one familiar scissors-type action within a small envelope of motion. The small motion envelope allows the applier to have a slender, elongated configuration which permits it to be used deep inside an incision site if necessary. The instrument includes elongated jaws which permit the clip and the vessel to be easily observed by the surgeon as the clip is introduced about the vessel and as it is set to ligate the vessel.

The present invention includes an elongated scissors-type handle and a cartridge which holds a large number of clips and which snaps into a cartridge-receiving channel located on the handle. The handle operates like a scissors with ring handles at one end and an elongated nose section at the other end. The nose section has jaws to which ligating clips may be fed automatically in rapid succession. Opening and closing the ring handles operates a mechanism associated with the handle to open and close the jaws and to provide a long stroke motion for feeding clips from the end of the cartridge to the nose section. Clips are indexed through the cartridge by reciprocating parts of the cartridge with respect to one another with a short stroke cocking motion captured from the long stroke motion. The drive motion for opening and closing the jaws and for providing the long and short stroke motion are all derived from the small envelope of motion of the normal opening and closing of the ring handles.

The jaws are opened and closed as follows. The handle includes a fixed handle body with one ring handle on one end and a fixed anvil jaw on the other end. A movable jaw member, with a movable jaw on one end and an extension arm at the other end, is pivotably attached to the handle body, at a point between the ends of the movable jaw member. A movable handle has a second ring handle on one end and a bore on the other end for pivotably attaching the movable handle to a cooperating pin on the movable jaw. The handle body includes a mechanism which operates under the influence of the movable handle to engage the extension arm portion of the movable jaw member to operate the jaws of the applier.

The movable handle and movable jaw member are attached to the handle body to pivot about the same point, and the mechanism for opening and closing the jaws includes an intermediate link with one end pivotably attached to the fixed handle body rearwardly of the movable jaw member and with the other end engaging the movable jaw member extension arm. A boss on the movable handle engages this intermediate link as the ring handle on the movable handle closes toward the ring handle on the fixed handle. Spring biasing is provided for the movable handle and movable jaw, so that they will automatically return to their initial positions when the user relaxes the grip on the ring handles. A cooperating slot and pin are used on the movable handle and the movable jaw, so that the jaws may be separated manually if the bias springs fail to return the jaws to the open position.

The long stroke motion for feeding clips from the cartridge to the jaws is provided by a cam pivotably mounted on the fixed handle, a pusher link with one end pivotably attached to the cam and the other end attached to a pusher by means of a pin which projects through a slot in the fixed handle. The pusher is located in the base of the cartridge-receiving channel. The cam is driven by an operative connection to the movable handle. Thus, as the movable handle opens and closes, the cam will rotate and drive the pusher back and forth in the cartridge-receiving channel. As the cam and its associated pusher link drive the pusher to its forwardmost position to deposit a clip in between the jaws, the cam and pusher link experience a toggle action to provide an extra push to make sure that the clip is properly positioned in the jaws.

The cartridge fits into the cartridge-receiving channel and clips may be removed from the first position in the cartridge and fed to the nose by the long stroke motion of the reciprocating pusher. A short stroke motion for indexing successive clips to the first position in the cartridge is captured from the long stroke motion by a cooperating slot and pin mechanism located on confronting elements of the pusher, the handle body and the cartridge. The cartridge-receiving channel on the handle body holds the cartridge adjacent the reciprocating pusher. The cartridge includes a fixed rack which does not move with respect to the handle body and a moving rack which reciprocates synchronously with the pusher in response to the captured short stroke motion.

In the preferred embodiment, the short stroke motion capture pin is located on the moving rack, and the short stroke motion capture slot is located on the pusher. A positive stop is provided by extending the pin on the moving rack into a precisely positioned slot on the main handle body to limit the forward motion of the pusher and control the location of the clip in the jaws and to control the length of the short stroke motion of the moving rack.

As will be explained in detail later in the application, the jaws are specially configured to (a) hold the clip so that the clip will not fall into the incision after it is deposited by the pusher and while it is waiting to be closed around a blood vessel; (b) so that the clip will not recede from the jaw tips as they are being closed about a blood vessel; and, (c) so that the clip will not be misaligned.

The cartridge provides a compact housing for a large number of clips. As a clip is indexed to the end of the cartridge, it is transferred from the plane of the stationary rack to the plane directly in front of the moving rack and then to the plane of the pusher. Thus, a clip can be indexed along the cartridge and advanced through three levels to the plane of the pusher and then fed to the nose where it may be set about a vessel. The forward end of the stationary rack includes a ramp slanting toward the plane of the pusher and transfer fingers for transferring the clips from one plane to another within the cartridge.

The long and short stroke motion and the closing action of the jaws are synchronized so that as the ring handles close, the pusher is first withdrawn from the nose section. After the pusher is almost completely withdrawn, the short stroke motion is captured from the motion of the pusher so that the short stroke motion capture pin on the moving rack engages the cooperating slot on the pusher to pull the moving rack rearward into position ready to index the clips forward one space. As the ring handles continue to close, the jaw closing mechanism engages and closes the jaws, but the pusher and its associated cam mechanism will dwell. As the user relaxes the grip on the ring handles, the jaws will open automatically under the influence of a bias spring. Further relaxation of the grip on the ring handles will permit the cam to move out of the dwell mode and start the pusher forward automatically under the influence of an additional bias spring. As the tip of the pusher approaches the first position of the cartridge, it will pick up a clip and automatically feed it to the nose section. When the pusher is almost all the way forward, the short stroke motion capture pin on the moving rack will engage the corresponding slot on the pusher to move the moving rack forward to index the clips forward one position. The forward motion of the moving rack and the pusher will stop when the short stroke motion capture pin hits against the forward edge of the stop slot in the main handle body. Although the detailed sequence of motion of a clip through the cartridge to the jaw tips is explained in detail later in this application, one can see from this summary that clips may be applied in rapid succession by merely tightening and relaxing the grip on the ring handles of the scissors-type applier and engaging the synchronized motions of the handle and cartridge mechanism. The user need not use unusual or uncomfortable manipulations but merely tightens the grip on the ring handles to fix a clip about a blood vessel and relaxes the grip to automatically open the jaws of the tool to automatically feed the next clip to the jaws and to automatically index the clips through the cartridge. The present invention provides a fast-acting, easy-to-use multiple ligating clip applier.

The preferred embodiment of the applier will be described in conjunction with clips which have a generally V-shaped configuration with a flexible hinge at the connecting point of the two legs of the "V". These clips include outwardly extending bosses located near the end of each leg of the "V".

The clip is slightly resilient outwardly so that when the clip is slid to the nose, the bosses will engage the jaw recesses so that the clip will be held in position even after the pusher is withdrawn prior to the time that the clip is set about a blood vessel and while the clip is being set about a blood vessel.

The jaws of the applier are offset in a plane below the plane of the main handle body to facilitate the entry of the pusher into the nose section. Each of the jaws include a U-shaped channel in which clips are guided to the tip of the jaws.

When using a clip without bosses, the natural resilience of the clip itself helps hold the clip between the open jaws of the applier. The jaws of the applier are equipped with channels which have carefully controlled dimensions so that there will be a slight frictional engagement between the sides of the clip and the jaw channels to further secure the clip in the jaws.

BRIEF DESCRIPTION OF THE DRAWINGS

These and other advantages and features of the present invention will become apparent from the following description of certain embodiments taken in conjunction with the following drawings in which:

FIGS. 3 and 4 show partial perspectives of the forward portions of the elements of the cartridge shown in FIG. 2;

FIGS. 3A and 4A show partial cross-sectional views of the elements of the cartridge shown in FIGS. 3 and 4 taken along section lines 3A—3A and 4A—4A, respectively;

FIG. 5 shows a plan view of the assembled handle portion of the present invention from one side;

FIG. 5A shows a cross-sectional view of the handle assembly shown in FIG. 5.

FIG. 5B shows a partial cross-sectional view of the handle with the cartridge in place;

FIG. 7 shows a cross-sectional, side elevational view of the cartridge of FIG. 2 assembled to the handle of FIG. 6 with the components arranged in a first position;

FIG. 8 shows a cross-sectional, side elevational view of the cartridge of FIG. 2 assembled to the handle of FIG. 6 with the components arranged in the second position;

FIG. 9 shows a cross-sectional, side elevational view of the cartridge of FIG. 2 assembled to the handle of FIG. 6 with the components arranged in a third position;

FIG. 10 is a side cross-sectional view of the jaws of the handle.

FIG. 11 is a front cross-sectional view of the jaw of FIG. 10; and,

FIG. 12 is a plan view of the jaw of FIG. 10.

DETAILED DESCRIPTION OF THE PREFERRED EMBODIMENT

Figure 1:
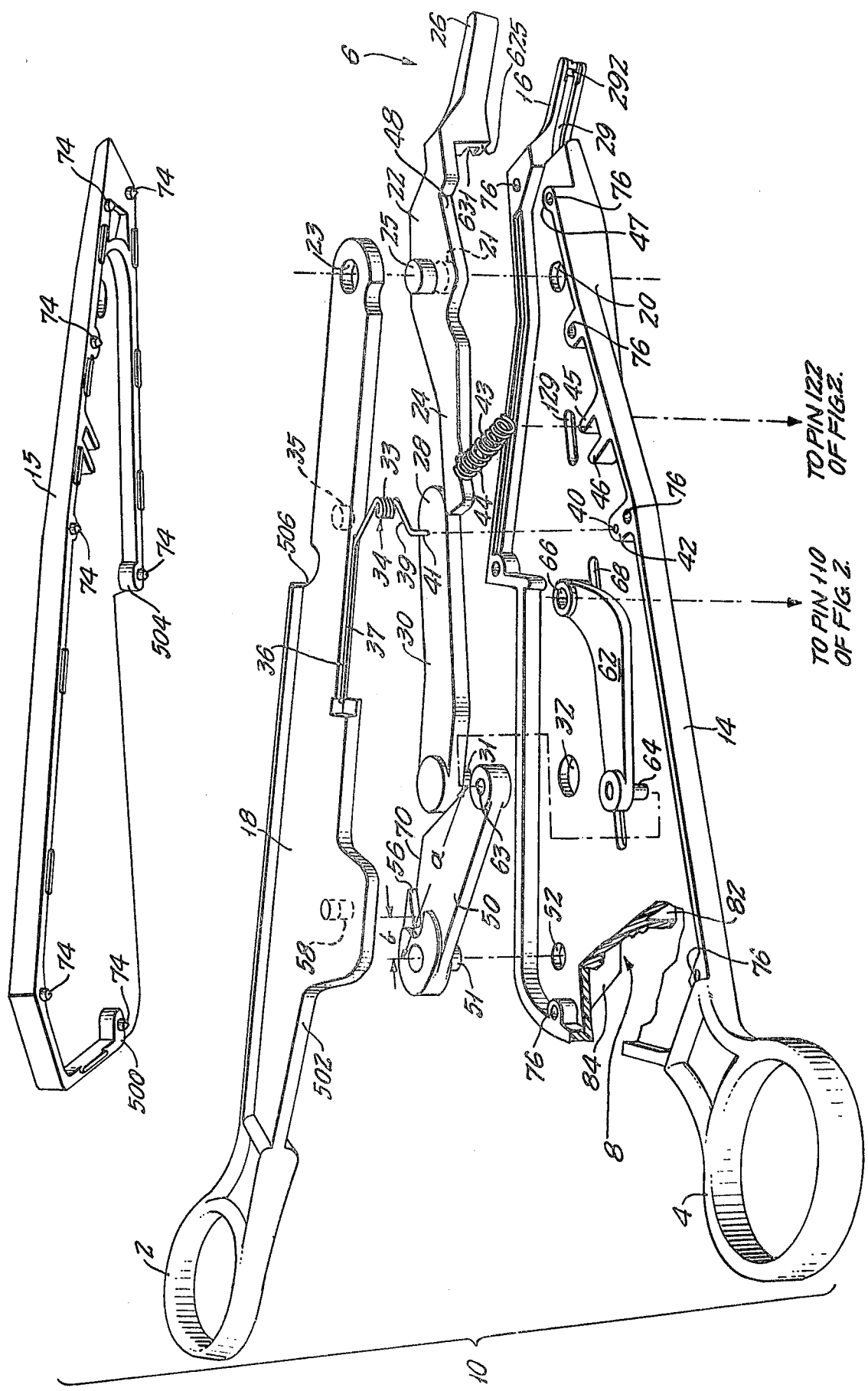
FIG. 1 shows an exploded perspective view of the handle portion of the present invention.
Figure 2:
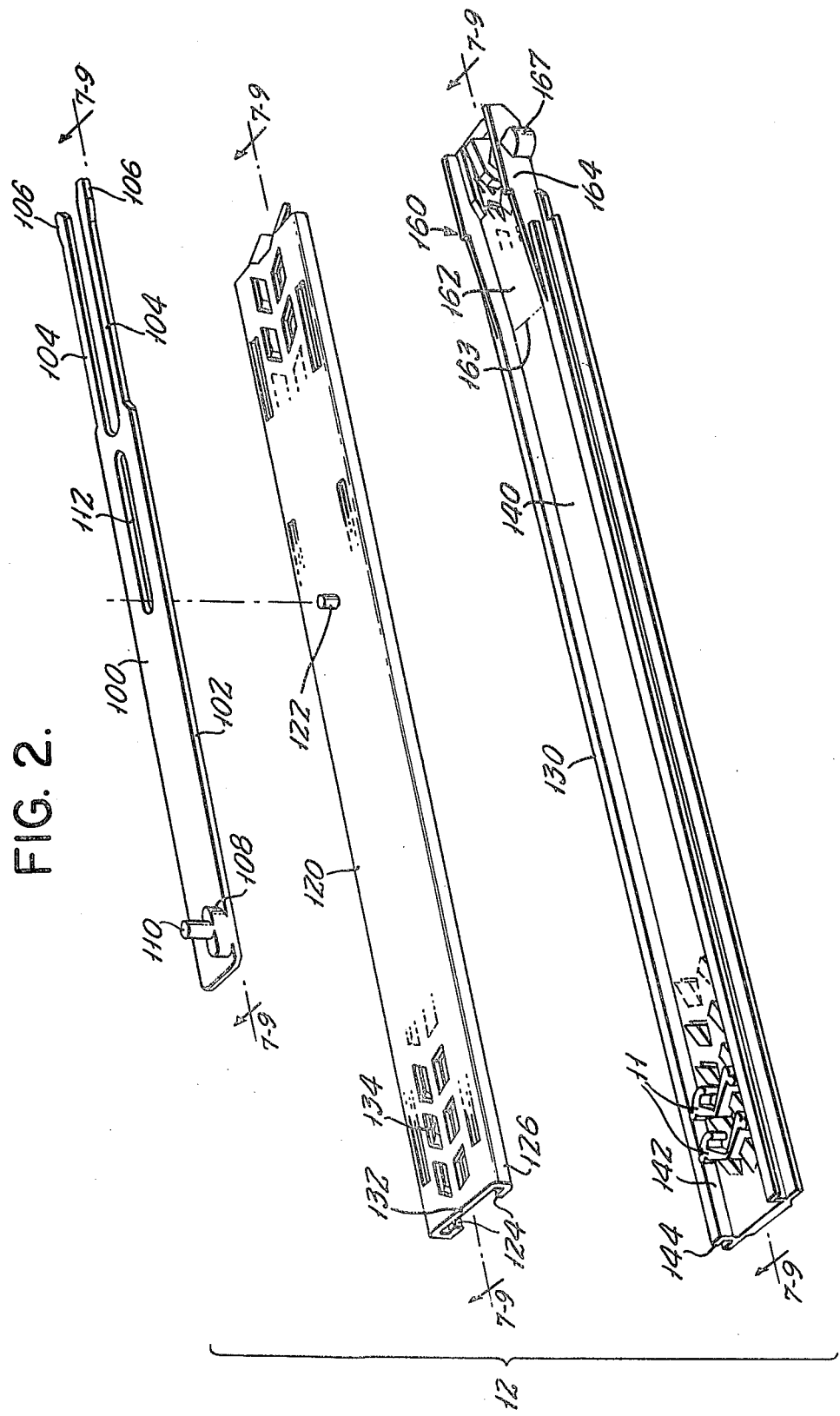
FIG. 2 shows an exploded perspective view of the cartridge of the present invention.

Referring now to FIGS. 1 and 2, there is shown an exploded perspective view of the multiple clip applier of the present invention, including a handle generally designated as 10 and a cartridge 12 which holds a large number of ligating clips 11 and which snaps into a cartridge-receiving channel 8 located on handle 10. The detailed structure of the forward end of the elements of cartridge 12 are shown in FIGS. 3, 3A, 4A and 4B. The handle 10 operates like an elongated scissors with ring handles 2 and 4 and an elongated nose 6 with jaws 16 and 26 to which ligating clips 11 may be fed in rapid succession.

The elongated configuration makes it easy for the user to reach into an incision to obtain access to a vessel to be ligated. The elongated nose section 6 may be slightly curved to one side and is offset below the plane of handle 10 to align the entrance to nose section 6 with cartridge 12 to facilitate the smooth delivery of clips 11 from cartridge 12 to nose section 6. The curved and offset configuration of nose section 6 allows the user to more easily observe a clip as it is being applied about a vessel. Opening and closing ring handles 2 and 4 operates the mechanism of handle 10, to open and close the jaws and to provide a long stroke motion for feeding clips 11 from the end of cartridge 12 to nose section 6 where they may be set about the vessel to be ligated. Clips 11 are indexed through cartridge 12 by reciprocating parts of the cartridge with respect to one another with a short stroke cocking motion captured from the long stroke feeding motion. These two motions are accomplished within the envelope of motion of the normal opening and closing of the ring handles to operate the jaws of the applier to set and deposit the ligating clip about a desired vessel. To set a clip about a blood vessel, the user tightens the grip on the ring handles and moves them together against the resistance of biasing springs. After a clip has been set about a blood vessel, the jaws can be automatically opened, and the next clip can be automatically fed into position in the nose section, and the remaining clips can be automatically indexed one step forward in the cartridge by relaxing the grip on the ring handles. The energy stored in the bias spring provides the automatic opening, feeding and indexing functions when the user relaxes the grip on the ring handles.

Either metal or plastic or absorbable plastic ligating clips can be used with the multiple clip applier of the present invention. This preferred embodiment has been designed to accommodate a two-legged clip joined by a resilient hinge, with the first leg of the clip terminating in a deflectable hook member adapted to engage the distal end of the second leg. (See FIG. 10.) As will be described in greater detail subsequently in the present application, each leg of the clip includes a raised boss 290 which engages corresponding depressions at the tip of each jaw to assist in holding the clip as it is being closed about a vessel. A suitable type of clip is disclosed in U.S. patent application Ser. No. 049,379, filed June 18, 1979, by Robert W. Mericle and assigned to the assignee of the present application. Although it has been found that clips of the kind described in U.S. patent application Ser. No. 049,379 work well with the multiple clip applier of the present invention, it is not intended that the scope of this invention be limited to a multiple clip applier for this clip alone or for any particular kind of clip.

Figure 6:
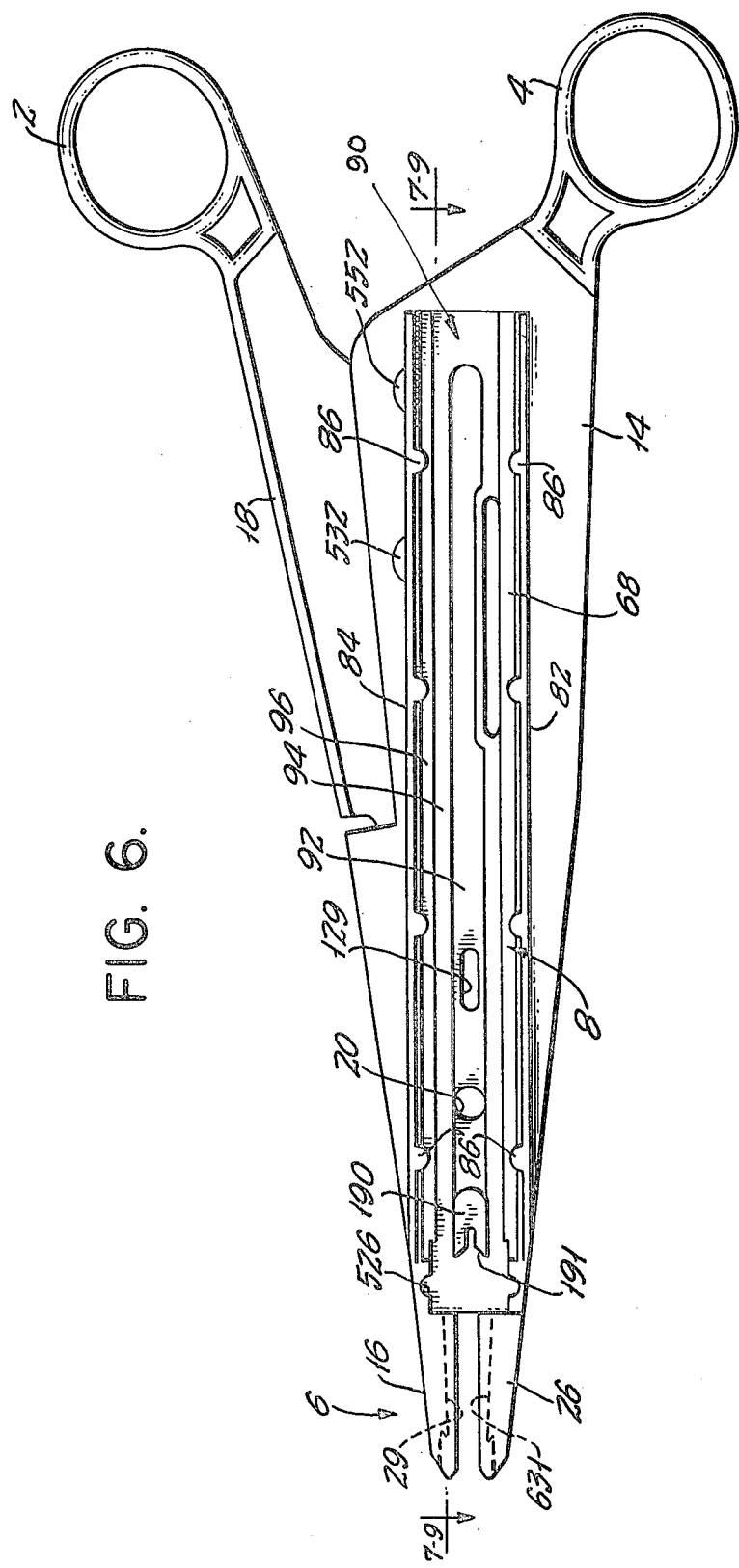
FIG. 6 shows a plan view of the assembled handle portion of FIG. 5 from the other side.

A description of the components of the handle mechanism will be set forth first in connection with FIGS. 1, 5 and 6. The jaw closing mechanism will be described first. Then the long stroke motion and mechanism for feeding clips to the nose will be described. This will be followed by a description of the components of the cartridge mechanism in connection with FIGS. 2 through 7. Then the cooperative operation of the mechanisms of handle 10 and cartridge 12 will be discussed in connection with FIGS. 7 through 12.

JAW CLOSING MECHANISM

As shown in FIG. 1, handle 10 inclues a main handle body 14 with a fixed ring 4 on one end and a fixed anvil jaw 16 on the other end and a central bore 20 extending through handle body 14. Movable jaw 22 includes a pivot pin 21 which fits into bore 20 to pivotably attach movable jaw 22 to main handle body 14. The distal end of movable jaw 22 incorporates a movable jaw tip 26 which may be moved toward anvil jaw 16 to set a clip 11. The proximal end of movable jaw 22 includes an extension arm 24 which extends rearwardly from pivot pin 21 toward ring handles 2 and 4. Extension arm 24 contacts and overlaps the distal end 28 of movable jaw closing link 30 which is pivotably attached to main handle body 14 by means of a cooperating pin 31 on the proximal end of link 30 and a bore 32 through main handle body 14. An additional thickness of material 532 is provided about bore 32 to afford additional strength in this area (see FIG. 6). Movable handle 18 includes a ring handle 2 on one end and a bore 23 on the other end. Bore 23 receives pin 25 to provide pivotable attachment of handle 18 to movable jaw 22. Pins 21 and 25 are coaxially aligned on opposed sides of movable jaw 22 so that movable jaw 22 and handle 18 pivot about the same point. Movable handle 18 includes a driven pin 35 which engages closing link 30 as ring handle 2 closes toward handle 4 to rotate link 30 clockwise about bore 32 so that distal end 28 engages extension arm 24 to cause movable jaw 22 to rotate counter-clockwise about bore 20.

The handle mechanism is biased using two springs. Torsion spring 34 provides a bias force to maintain ring handles 2 and 4 biased open. Torsion spring 34 includes a number of generally circular coils 33 (preferably four) aligned about a common axis and a first leg 37 and a second leg 39, both extending generally tangentially from coils 33. The end of the second leg 39 is bent at a sharp angle to form a holding pin 41. Holding pin 41 is mounted in a hole 40 in a boss 42 on main handle body 14. First leg 37 of spring 34 engages a slot 36 in movable handle 18. Part of the energy exerted by the user in closing ring handles 2 and 4 is stored in torsion spring 34 to be used to automatically restore the ring handles to the open position when the user relaxes the grip on ring handles 2 and 4.

It should be noted that as ring handles 2 and 4 open and close against the bias of torsion spring 34, the coil portion 33 of spring 34 can float with respect to main handle body 14 so that the opening and closing action is smooth.

Compression coil spring 43, supported on stem 44 mounted near the proximal end of extension arm 24, is held in place between projections 45 and 46 on main handle body 14 and provides a bias force to maintain jaws 16 and 26 biased open. Since extension arm 24 contacts movable jaw closing link 30, compression spring 43 also biases link 30 in the counter-clockwise direction.

The maximum distance between movable jaw tip 26 and fixed anvil jaw tip 16, in the fully open position, is controlled by stop 47 on main handle body 14 forward of pivot bore 20 and a corresponding notch 48 on movable jaw 22. Coil spring 43, rearward of pivot bore 20, biases movable jaw notch 48 against stop 47 to control the maximum open position of jaw tips 16 and 26. Closing link 30 rests against the confronting surface of extension arm 24 of movable jaw 22 but does not directly experience the bias force of coil spring 43 when movable jaw 22 is in the fully open rest position.

Surface 502 of movable handle 18 will contact and stop against stop 500 on cover 15 to control the fully closed position of ring handles 2 and 4. The fully open position of ring handles 2 and 4 is controlled by a stop 504 on cover 15 which contacts notch 506 on movable handle 18.

The linkage for opening and closing the jaws is particularly useful because it provides strong, smooth force transmission and a relatively wide jaw opening with a limited amount of travel of ring handle 2 with respect to ring handle 4. In the most open position, ring handles 2 and 4 may be easily grapsed by the user's hand. In the most closed position, ring handle 2 still maintains a significant distance from ring handle 4 so that the user is not forced to close his hand an unusual amount. As will subsequently be explained in detail, a part of the closing action of ring handles 2 and 4 is used to provide a long stroke feeding motion for feeding clips 11 to nose 6 and a short stroke cocking motion for indexing clips 11 through cartridge 12, and part of the closing action of ring handles 2 and 4 is used to close jaws 16 and 26. Since all of these motions are derived from the scissors action of the ring handles, it is important that the handle mechanism transmits the motion smoothly, with smooth transitions between the various synchronized motions, so that the user does not experience a jerking or uneven motion as the ring handles operate. The use of two separate bias springs, torsion spring 34, and coil spring 43, and the floating disposition of torsion spring 34 facilitate this smooth action. Thus, the surgeon is able to set the clip within the familiar envelope of motion of an ordinary scissors.

CLIP DELIVERY MECHANISM

The driving action for feeding a clip from cartridge 12 to nose section 6 and for indexing a clip through cartridge 12 will now be discussed. The elements which provide the long stroke driving action for feeding a clip from cartridge 12 to nose section 6 are housed on the handle body. The part of the motion for feeding a clip 11 through cartridge 12 is captured from the long stroke feeding motion by a pin and slot mechanism positioned partly on the feeding mechanism and partly on the cartridge itself. The elements for the long stroke delivery motion will be discussed first.

Cam 50 is pivotably attached to main handle body 14 by a cooperating pin 51 on cam 50 and pivot bore 552 through handle body 14. An additional thickness of material 52 is provided about bore 52 to afford additional strength in this area (see FIG. 6). Cam 50 includes a complex cam surface 56. A boss 58 on movable handle 18 which engages complex cam surface 56. A bore 63 through cam 50 receives pin 64 on pusher link 62. The other end of pusher link 62 includes a bore 66 which receives pusher pin 110 (see FIG. 2). Pin 110 projects through a pusher slot 68 which extends generally longitudinally along main body handle 14. Pin 110 is connected to pusher 100, which rides in channel 8 on handle body 14 for placing clips 11 between jaws 16 and 26, as will be explained in connection with FIGS. 7 to 9. It can be seen from FIG. 1 that as ring handle 2 closes toward ring handle 4, boss 58 will tend to move cam 50 clockwise about pivot pin 51 so as to pull the proximal end of pusher link 62 and correspondingly pusher pin 110 rearwardly on a rather long stroke. Complex cam surface 56 of cam 50 hooks around boss 58 so that the bias provided to movable handle 18 by torsion spring 34 is transmitted to cam 50 and, thence, to pusher link 62 so that pusher link 62 is biased forward. Complex cam surface 56 has a dwell portion 70 which permits movable handle 18 to continue to close and activate the jaw tips 16 and 26 after pusher pin 110 has retracted all of the way to the back of pusher slot 68.

The delivery of a clip to the nose is completely automatic and occurs merely by having the user relax the grip on the ring handles 2 and 4.

As the user relaxes the grip on ring handles 2 and 4, they will open again under the influence of bias spring 34. Cam 50 will dwell while jaw tips 16 and 26 are opening. When the dwell ends, boss 58 will then enter complex cam surface 56 and start cam 50 rotating counter-clockwise to drive pusher link 62 and, correspondingly, pushers 100 forward still undler the influence of bias spring 34. As ring handles 2 and 4 approach the fully open position, the force exerted by bias spring 34 tends to diminish so that pusher 100 may not be driven forward with sufficient force to complete the placement of a clip 11 in the proper position in nose 6. At the same time, the force needed to operate the mechanism increases. For example, additional force in needed to push moving rack 120 forward and to index the clips 11 forward one position against the combined resistance of the several fingers 134. Additional force is also needed to push the clip into the jaws and to partially close clip 11 as it proceeds to the nose. To provide the necessary force, cam 50 is designed like a toggle to give a slight push to link 62 just as pusher 100 is approaching its forward-most position. This toggle action is accomplished when pivot points 52, 63 and 66 line up essentially in a straight line and provide an extra push at the end of the forward motion of pusher 100. Slot 68 must be long enough so that pin 110 will not jam on the end of slot 68 before the toggle action occurs.

The distance between the center of rotation of pivot pin 51 and complex cam surface 56 (distance "b" in FIG. 1) and the distance between the center of rotation of pivot pin 51 and the center of bore 63 (distance "a" in FIG. 1) has a ratio of preferably 4 to 1 (i.e., $a/b = 4/1$).

This ratio improves the smoothness of the drive motion and facilitates a smooth transition between the various actions of the handle mechanisms in driving pusher link 62 on a long stroke motion, closing the jaws, and setting the clip.

Initially, a relatively large force is required to drive cam 50 and link 62. Once the cam enters the dwell mode, this force drops. With a large cam ratio, a large force is required to move cam 50. By reducing the cam ratio to about 4 to 1, sufficient force is supplied to keep the motion smooth but not so much as to make the handles hard to close.

As previously explained, the ability of coil 33 of torsion spring 34 to float as the ring handles 2 and 4 move further facilitates the smooth action of the drive mechanism.

The movable jaw 26, movable handle 18, jaw closing link 30, cam 50 and pusher link 62 are all disposed on one side of main handle body 14 and are covered and held in place by cover 15, which is attached to main handle body 14 by a number of pins 74 which fit into bores 76 disposed about the periphery of main handle body 14. Pins 74 may be bonded into bores 76 or some suitable alternative made of fixing cover 15 on main handle body 14.

Referring now to FIGS. 1, 5A, 5B, and 6, generally U-shaped channel 8 extends generally longitudinally along the other side of main handle body 14 and is bounded by upstanding walls 82 and 84. As shown in FIGS. 5B and 6, each upstanding wall 82 and 84 includes a series of snap-fit tabs 86 for receiving the elements of the cartridge with a snap-fit to hold it in position. The base 90 of U-shaped channel 8 includes a first centrally disposed axially running recess 92. Base 90 of channel 8 steps up to a first step 94 and a second step 96 whose function will be explained in connection with cartridge 12.

Referring again to FIG. 2, an elongated pusher 100 is used to feed clips 11 from the end of cartridge 12 to nose section 6. Pusher 100 is shown approximately in the position it is shown in FIG. 9, extending forward of the other elements of cartridge 12 on its way to nose 6. Pusher 100 is an elongated element with a rearward body section 102 whose edges fit into the first step 94 in base 90 of U-shaped channel 8 (see FIG. 5B). Body section 102 of pusher 100 includes a pusher pin base 108 which supports a pusher pin 110. Pusher pin 110 extends generally perpendicular to the plane of pusher 100 and is adapted to fit into a bore 66 in pusher link 62. Thus, pusher 100 slides back and forth on step 94 of channel 8 with pusher pin 110 slides back and forth in slot 68 as ring handles 2 and 4 open and close. Pusher pin 110 provides the connection between the long stroke driving motion of pusher link 62 and pusher 100 to provide the means for feeding clips 11 from cartridge 12 to nose section 6 of handle 10.

Turning now to FIG. 2, body section 102 of pusher 100 includes a centrally located axial ratchet slot 112. Ratchet slot 112 cooperates with a pin 122 mounted on moving rack 120 of cartridge 12 to provide the reciprocating short stroke motion for indexing clips 11 through cartridge 12, as will be subsequently explained in greater detail.

Fingers 104 extend forwardly from body section 102 and terminate in a beveled tip 106 which is beveled at an angle corresponding to the angle between the legs of the hinged clips which, as has been previously explained, have been chosen to illustrate this preferred embodiment of the multiple clip applier of the present invention. Fingers 104 pick up a clip 11 as it exits from cartridge 12 and feeds it to nose section 6.

FIG. 1 shows that nose section 6 is stepped sufficiently below the plane of main handle body 14 to permit pusher 100 to slide directly out of channel 8 into nose 6 as it moves forward to feed clips 11 to jaws 16 and 26. Step 625 drops movable jaw 26 below the plane of main handle body 14. A corresponding step (not shown in FIG. 1) drops the plane of anvil jaw 16 below the plane of main handle body 14 so that jaws 16 and 26 are aligned with one another. Jaws 16 and 26 have oppositely facing U-shaped channels 29 and 631 for receiving clips 11. It can be seen that step 625 and its corresponding step on jaw 16 drop the entrance to U-shaped channels 29 and 631 sufficiently below the plane of main handle body 14 to permit pusher 100 to extend directly into the channels 29 and 631 from cartridge 12.

The ends of jaws 16 and 26 must be adapted to conform to the geometry of the clip, for example, the clip which is used to illustrate the preferred embodiment of this multiple clip applier has raised bosses 290 on each of its legs which engage corresponding recesses 292 at the tip of each jaw (see FIGS. 10–12). The raised bosses 290 are located near the end of each leg and face outwardly in the plane defined by the V-shaped clip. Pusher 100 pushes clips forward into the jaws until bosses 290 drop into recesses 292.

JAW TIP CONFIGURATION

Referring to FIG. 10, there is shown an enlarged view, partly in section of jaw tip 26 showing the details of the tip. Jaw tip 16 is the same as jaw tip 26 and is shown only in FIG. 11.

The channels 29 and 631 have a constant width such that clips may slide easily out to the end of jaws 16 and 26. However, the jaws are configured so that in the fully opened position, the base of channel 631 tapers slightly toward the similar base (not shown) of channel 29 so that the transverse dimension from the base of channel 29 to the base of channel 631 decreases as the clip proceeds toward the tip so as to compress and partially close the clip as it is delivered to the end of the jaws. This has the advantage of using the spring action of the resilient hinge of the clip itself to assist in holding the clip in the jaws and also to partially close the clip so that less motion is required on the part of the user to completely set the clip about a vessel. This spring action helps bosses 290 snap into recesses 292 to properly locate a clip in the jaw tips 16 and 26.

The very forward portion of the walls of U-shaped channels 29 and 631 include convex curvatures 522 and 524 which are used to make sure that even if the jaw tips are somewhat misaligned, the clips will still close correctly (see FIG. 11).

The base 520 of channel 29 and the base of channel 631 each have a recess 292 for receiving boss 290. Recess 292 undercuts the base of channel 631 so that the recess and the base form a sharp angle. Recess 292 extends axially a distance greater than the thickness of boss 290 and then curves into a stepped down exit portion 528 of base 520. The undercut portion of recess 292 deters the rearward motion of clip 11 as it is being closed around a blood vessel so that the clip will not recede as it is closed and possibly improperly ligate the vessel. Stepped down exit portion 528 makes it easier for a clip to escape from the jaws after it has been closed about a blood vessel and provides clearance to permit the clip to latch. The axial length of recess 292 is greater than the thickness of a clip boss 290 so that the clip will engage recess 292 even if the dimensional tolerances on the various moving parts cause pusher 100 to slightly overshoot or undershoot recess 292.

Fingers 104 of pusher 100 are able to deflect to follow tapering channels 29 and 631 as a clip 11 is pushed between jaws 16 and 26. Successive flexing of fingers 104 as they are moved in and out of the jaws to deliver successive clips may cause the fingers to lose some of their resiliency and not return to their fully opened position. If the fingers are not in their fully opened position when they start to push a clip into the nose section, the clip may become misaligned and jam.

Referring to FIG. 6, an upstanding boss 190, mounted on base 90 of channel 8, is used to spread the fingers 104 back to their original transverse separation, as pusher 100 retracts from the nose back into channel 8. Boss 190 is located toward the forward end of channel 8 and has a diameter aproximately equal to the transverse distance between fingers 104 of pusher 100. The edges of boss 190 are spaced apart from the side walls 82 and 84 of U-shaped channel 8 a distance slightly greater than the width of fingers 104. Boss 190 is positioned such that as pusher 100 is retracted from nose section 6, fingers 104 will be spread apart to their original spacing. Boss 190 also has a forward facing V-shaped cutout 191 to receive and properly position a clip 11 so that it may be more easily picked up by pusher 100 as it moves forward into nose section 6.

CARTRIDGE MECHANISM

The components of the cartridge and the way in which they interact with the drive mechanism on handle 10 and the way in which they fit into U-shaped channel member 8 will now be described in connection with FIGS. 1, 2, 3, 3A, 4, 4A, 5B and 6.

Referring to FIG. 2, cartridge 12 includes to basic elements: moving rack 120, and fixed rack 130 between which is housed a plurality of clips 11.

Referring to FIGS. 2 and 4, moving rack 120 is a generally U-shaped channel having inwardly projecting rails 124 affixed to side walls 126 and recesses 125 at the inside portion of the base of side walls 126. Rail 124 may extend along the entire extent of wall 126 or may be intermittent to facilitate fabrication. Rack 120 may be stamped metal or molded plastic or some other suitable material. Base 132 of moving rack 120 includes a large number of sets of flexible fingers 134 which extend along moving rack 120 and project into the space defined by the U-shaped configuration of moving rack 120. These fingers 134 may be molded into base 132 or may be stamped into a separate piece of metal which can be bonded to base 132. The forward-most set of fingers 134 extend a short distance beyond the end of base 132 and the end of side walls 126 as shown in FIG. 4A.

Referring again to FIG. 2, ratchet slot 112 of pusher 100 is adapted to receive ratchet pin 122 projecting from moving rack 120 to provide a means of using a portion of the long stroke motion of pusher 100 to provide a short stroke reciprocating motion for indexing clips between moving rack 120 and fixed rack 130.

Referring to FIGS. 1 and 2, ratchet pin 122 projects through ratchet slot 112 in pusher 100 into slot 129, located centrally on main handle body 14. The function of slot 129 is to limit the forward motion of pusher 100 and moving rack 120. When pin 122 hits the forward end of slot 129, pusher 100 and moving rack 120 will stop. By carefully controlling the distance from the forward end of slot 129 to recess 292 in jaw tips 16 and 26 and by controlling the distance from pin 122 to the end of pusher 100, one can be assured that clip bosses 290 will engage jaw tip recess 292.

The axial length of slot 129 also controls the maximum distance that moving rack 120 will move back and forth, as will be explained later.

Referring now to FIGS. 2 and 3, fixed rack 130 is generally U-shaped channel with a base 140 and side walls 142. The upper edge of each side wall 142 includes an outwardly extending rail 144 over which rails 124 of side wall 126 of moving rack 120 snap to form an enclosed cartridge for clips 11. As can be seen best in FIG. 5B, rails 144 snap into recess 125 at the base of wall 126. The upper surface of wall 142 of fixed rack 130 engages the confronting surface of base 132 of moving rack 120 so that moving rack 120 may reciprocate on a short stroke motion back and forth with respect to fixed rack 130. The base 140 of fixed rack 130 houses a similar plurality of flexible fingers 134 which project into the space defined by the U-shaped configuration of fixed rack 130. A plurality of clips 11 are placed along the base of fixed rack 130 separated by fixed rack fingers 134. As can be seen best in FIGS. 7 to 9, the flexible fingers 134 projecting respectively from moving rack 120 and fixed rack 130 slightly interfere with one another so that as moving rack 120 moves backwards, its fingers will deflect and ride over clips 11 and the spring back behind clips 11. The fingers on fixed rack 130 prevent the clip from being drawn backwards with the backward motion of moving rack 120. As moving rack 120 goes forward, it will index the clips forward one position. Thus, the short stroke reciprocating motion of moving rack 120 with respect to fixed rack 130 provides an indexing action for feeding clips through cartridge 12 to the first position on fixed rack 130.

In FIGS. 3, 3A and 7, the forward-most set of fingers on fixed rack 130 are labeled 134b. Positioned between set 134b is a transfer finger 200 which is longer than the other fingers 134 and is specially configured. As shown in FIG. 3A, transfer finger 200 includes a three-faceted surface 530 which tapers in three facets to transfer clips from the plane of fixed rack 130 to the plane of step 94 in cartridge receiving channel 8 on which pusher 100 rides. In the preferred embodiment, the first facet of surface 530 forms an angle of about 35° with base 140 of fixed rack 130, the second facet has about a 16° angle and the third facet has about a 7° to 8° angle. Transfer finger 200 acts like a spring, and three-facet surface 530 acts as a guide for clips 11. As will be explained in greater detail in conection with FIGS. 7, 8 and 9, transfer finger 200 transfers clips 11 from one level to another within cartridge 12 to assist in feeding clips 11 to nose section 6.

Having explained the reciprocating short stroke mechanism for indexing clips 11 through cartridge 12, we will now explain the apparatus for transferring clips 11 from inside cartridge 12 into channel 8 and depositing the clips in front of pusher 100 for delivery to nose section 6.

Still referring to FIGS. 3 and 3A, the forward section 160 of fixed rack 130 defines an extension for the U-shaped channel defined by fixed rack 130. The base 162 of forward section 160 forms a ramp tapering toward handle body 14. The ramp extends in a plane from end line 163 of base 140 to the end of forward section 160. Side walls 164 of forward setion 160 extend generally parallel to corresponding side walls 142 of fixed rack 130 to the end of forward section 160. Portion 168 of the bottom edge of side walls 164 extends generally parallel to ramp 162 from end line 163 to a step 165.

Portion 170 of the bottom of side wall 164 extend from step 165 to the end of forward section 160 generally parallel to the plane defined by rails 144 but is offset slightly closer to main handle body 14. As will be explained later in connection with the operation of the cartridge, portion 170 provides a guide for the forward motion of fingers 104 of pusher 100.

A pair of ribs 560 are positioned on ramp 162 inside portions 170 of wall 164 to help guide clips 11 as they are transferred from the plane of motion of pusher 100. Ribs 560 rise in a first section 562 to a land portion 564.

The very forward portion of ribs 560 taper at a further angle toward the plane of pusher 100 to form wedges 566 to assist in the smooth delivery of a clip into the nose section 6 of handle 10.

Cartridge 12 snap-fits into channel 8 and is aligned to provide smooth transfer of clips 11 along channel 8 and thence to nose 6. Locating bosses 167 on the outsides of side walls 164 mate with corresponding recesses 526 (see FIG. 6) in main handle body 14 to locate fixed rack 130 in a proper axial position in cartridge receiving channel 8. Returning to FIG. 3, extending from base 140 of fixed rack 130 are flanges 150 which extend beyond the periphery of rails 144. The edge 152 of flanges 150 snap under snap tabs 86 in side wall 82 and 84 to hold cartridge 12 in U-shaped channel 8 (see FIG. 5B).

Thus, it can be seen from FIG. 5B that side walls 142 of rack 130 snap inside side wall 126 of moving rack 120 to house a plurality of clips 11 between the fixed rack 130 and moving rack 120. As shown in FIGS. 5B and 8, the forward section 160 of rack 130 extends beyond the end of moving rack 120 so that portion 170 of the bottom of side wall 164 is aligned in substantially the same plane as step 96 of channel 8.

As shown in FIGS. 5B and 9, pusher 100 rests on the first step 94 in the base 90 of U-shaped channel 8 with pin 110 projecting into bore 66 of pusher link 62. The assembled cartridge of moving rack 120 and fixed rack 130 snaps it U-shaped channel 8 as flanges 150 snap into tabs 86. When the assembled cartridge is in position in U-shaped channel 8 surface 133 of moving rack 120 rests slidably against the second step 96 of base 90 of U-shaped channel 8 and moving rack drive pin 122 fits into moving rack slot 112 on pusher 100 and projects into slot 129 on main handle body 14.

PROGRESSION OF A CLIP THROUGH THE CARTRIDGE TO THE NOSE

The progression of a clip 11 through cartridge 12 to nose 6 will now be traced in connection with FIGS. 1 and 2, and three sequence drawings, FIGS. 7, 8 and 9, showing the operative parts of the cartridge in three different positions as a clip 11 is advanced from cartridge 12 into nose section 6. As clips 11 progress from between fixed rack 130 and moving rack 120 to nose section 6, each clip proceeds through three separate levels in the cartridge. At the first level the clip is maintained between the confronting surfaces of fixed rack 130 and moving rack 120. (See clip 11 in FIG. 7.) As a clip is advanced along fixed rack 130, it moves to a second plane directly in front of moving rack 120 where it is held in position against the adjacent surface of pusher fingers 104 by special transfer finger 200 extending from fixed rack 130. (See clip 11c in FIG. 7.) As pusher 100 is withdrawn from the nose section 6 so that clip 11d in FIG. 7 may be set about a vessel, clip 11c will be transferred to a third level in the plane directly in front of pusher 100 by transfer fingers 200 in position ready to be delivered to the jaws. (See clip 11c in FIG. 8.)

The sequence of action of handle 10 that causes clips to be advanced from position 11a to 11d will now be discussed in conjunction with FIGS. 5, 7, 8 and 9.

Referring now to FIG. 5, the multiple clip applier of the present invention is shown in the rest position with the ring handles 2 and 4 held all the way open by spring 34. Correspondingly, jaw tips 16 and 26 are also all the way open, and pusher link 62 is all the way forward in pusher slot 68 so that fingers 104 of pusher 100 are extended all the way into channels 29 and 31. As shown in FIG. 7, clip 11d is placed at the end of nose section 6 ready to be set about a vessel. Still referring to FIG. 7, with pusher 100 in the forward position, the rearward edge of pusher slot 112 engages ratchet pin 122 on rack 120 and pulls rack 120 forward with pusher 100. Moving rack 120 will move forward until pin 122 engages the forward end of slot 129.

As moving rack 120 comes forward, it will advance all of the clips 11 on fixed rack 130 forward one position. Clip 11c will now be in the forward position on fixed rack 130 with the hinge portion of the "V" shaped clip underneath transfer finger 200. The ends of "V" shaped 11 adjacent bosses 290 are supported on ribs 560. The plane section 562, land section 564 and wedge section 566 guide the edges of the clip as it is transferred from the plane of fixed rack 130 to the plane of pusher 100. In FIG. 9, forward-most clip 11c will be prevented from moving backwards by fingers 134b on fixed rack 130. Forward most clip 11c in FIG. 9 is now in position ready to be placed in front of pusher fingers 104 when pusher 100 is withdrawn.

Referring now to FIG. 8, the position of the operative parts of cartridge 12 is shown with ring handles 2 and 4 closed sufficiently to retract pusher 100 and moving rack 120, with clip 11d held between jaw tips 16 and 26 ready to be set about a vessel to be ligated. Referring first to the handle mechanism shown in FIGS. 1 and 5, one can see that as one starts to close ring handle 2 toward ring handle 4, cam boss 58, which is affixed to movable handle 18, will cause cam 50 to rotate clockwise about cam pivot bore 52 so as to move pusher link 62 rearwardly in pusher slot 68 and, correspondingly, to retract pusher 100 out of nose 6 leaving clip 11d at the tip of jaws 16 and 26 in the open position and with bosses 290 resting in boss retainer recesses 292. The curved configuration of nose 6 offsets the tips of nose 6 so that the clip may be more easily seen by the user when the clip is in position ready to be closed around the vessel. When pusher 100 is almost all the way back, ring handle 2 has closed toward ring handle 4 a sufficient amount to permit projection 35 on movable handle 18 to engage movable jaw closing link 30 and to cause it to pivot in a clockwise direction about pivot bore 32. The proximal end 28 of link 30 engages extension arm 24 of movable jaw 22 and causes movable jaw 22 to rotate counter-clockwise about pivot bore 20 and close jaw tip 26 toward anvil jaw 16 and set clip 11d about a vessel.

Referring now to FIG. 8, one can see that as ring handle 2 continues to close toward ring handle 4, pusher fingers 104 will move all the way back rearwardly of clip 11c and transfer finger 200 will transfer clip 11c to the plane of pusher 100 directly in front of pusher 100. The V-shaped recess tips 106 of pusher fingers 104 will engage the corresponding V-shape of clip 11c so that, as previously explained, when pusher 100 moves forward again, the clip will be maintained in its partially opened position so that it will not jam as it is tranferred forward.

Still referring now to FIG. 10, one can see that as pusher 100 recedes all the way back, the forward end of ratchet slot 112 in pusher 100 will engage ratchet pin 122 on moving rack 120 and draw moving rack 122 rearwardly behind clip 11b. The adjacent fingers 134 of fixed rack 130 will prevent clip 11b from receding with moving ratchet 120.

Moving rack 120 will continue to be drawn rearward with the rearward travel of pusher 100 until pin 122 engages the rearward end of slot 129 (see FIG. 10). At this point cam 50 (see FIG. 1) will enter dwell portion 70 so that as one continues to close ring handles 2 and 4 to set clip 11d, the operative parts of cartridge 12 will remain stationary.

Referring now to FIGS. 1 and 9, one can observe the operative parts of cartridge 12 as ring handles 2 and 4 are opened automatically under the influence of bias spring 34 when the user relaxes the grip on the handles after clip 11d has been set about a vessel. As ring handle 2 moves away from ring handle 4, projection 35 will move away from link 30 and permit link 30 to rotate counter-clockwise under the influence of biased spring 34 and, correspondingly, to permit movable jaw 22 to rotate clockwise about pivot point 20 under the influence of spring 43 to open jaw 26 away from anvil jaw 16 and release the closed clips. As the user continues to release ring handle 2 away from ring handle 4, cam 50 will come out of the dwell mode and begin to pivot in the counter-clockwise direction about pivot bore 52 so as to drive pusher link 62 forward in pusher slot 68 and, correspondingly, to drive pusher 100 forward into nose 6. As the handles continue to open and pusher 100 moves forward, beveled tips 106 of fingers 104 will engage the back of clip 11c and start it moving forward into nose section 6. As pusher 100 continues forward, the rearward edge of slot 112 on pusher 100 will engage ratchet pin 122 and move rack 120 forward to drive clip 11b from fixed rack 130 under transfer finger 200. Clip 11b is urged against the confronting surface of fingers 104, ready to drop into position in front of pusher 100 when the pusher is withdrawn the next time handle 2 closes toward handle 4. It can be seen that a plurality of clips 11 may be advanced forward through cartridge 12 to nose 6. The clips may set in rapid succession to ligate a large number of vessels quickly and efficiently.

Thus the reciprocating motion of moving rack 120, with respect to fixed rack 130, will advance clips through cartridge 12 from the first plane of the clips in fixed rack 130 to the second plane directly in front of moving rack 120. The ratcheting motion is synchronized to the action of pusher 100 so that the hinge portion of "V" shaped clip will be sandwiched between pusher 100 and transfer finger 200 when the pusher is all the way forward. The ends of "V" shaped clip will rest on ribs 560. When the pusher withdraws, transfer finger 200 will transfer the forward-most clip to a third level within the cartridge directly in front of the pusher 100 ready to be advanced to nose section 6.

The long stroke motion of pusher 100 provides the means for feeding clips from the forward-most position in fixed rack 130 to nose section 6. The interaction of ratchet slot 112 and ratchet pin 122 allows a portion of this long stroke motion to be captured to provide the short stroke ratcheting motion for moving rack 120 for indexing clips through cartridge 12. The interaction of pin 122 and its corresponding slot 129 provide positive stops for providing exactly the right stroke length to permit clips to be advanced through the cartridge in the right sequence and to provide a positive stop for the forward motion of pusher 100.

The last clip in each cartridge is a lockout clip specially designed to jam the mechanism to provide an indication to the user that the cartridge is empty. The lockout clip is a rigid metal clip which will advance only into the beginning of channels 29 and 631 of jaws 16 and 26. If pusher 100 attempts to push this rigid metal clip further into the jaws, the lockout clip will bind. This specially designed lockout clip is also colored a different color from the remainder of the clips so that the user can easily observer through a transparent portion of fixed rack 130 that he is using the last clip.

While the present invention has been described in connection with certain preferred embodiments, those skilled in the art will appreciate that certain modifications may be made without departing from the scope of the present invention. It is, therefore, not intended that the present invention be limited except as set forth in the following claims.

We claim:

1. Jaw tips for a medical instrument for applying ligating clips comprising:
   a right and left jaw disposed in confronting relationship and adapted to move together to close a clip about a vessel to be ligated, each of said jaws including:
   a generally U-shaped channel having a first and second side wall and a base, the base of each jaw tapering toward the other as one advances in a direction toward the jaw tips from the body of said instrument when said jaws are in the fully opened position to partially close a clip as it is delivered to the jaw tips to assist in maintaining the clip within said U-shaped channels;
   the distal end of each jaw tip including a recess for receiving a projecting portion of said clip and for retaining said clip projection therein during closing, thereby preventing said clip from receding into said U-shaped channels as it is closed about a vessel;
   said recess including a first portion which undercuts the base of each said U-shaped channel, the base and the edge of the recess forming an acute angle to provide a stop for preventing the clip from receding from the jaws while it is being closed about a vessel to be ligated, the bottom of said recess extending longitudinally of its jaw a distance greater than the projecting portion of said clip to facilitate the entry of the projecting portion on said clip into said recess;
   each said jaw tip further includes a planar exit portion stepped down below the plane of said U-shaped channel bases and extending from the distal end of each said recess to the distal end of each said jaw tip;
   the inwardly facing, upper portion of each side wall of each said U-shaped channel includes a convex, curved portion extending longitudinally along said U-shaped channel from a point rearward of said recess to the end of each jaw tip to facilitate proper closure of the ligating clip despite misalignment of said jaw tips.

2. The jaw tips of claim 1 further including a tapered end portion for each of the upstanding side walls of each U-shaped channel extending from a point forward of said recess to the distal end of said jaw tip to facilitate sighting of a clip as it engages a vessel to be ligated.

3. Jaw tips for a medical instrument for applying a plurality of ligating clips comprising:
   a generally U-shaped channel having a first and second side wall and a base, the base of each jaw tip tapering toward one another as one advances in a direction toward the jaw tips from the body of said instrument when said jaws are in the fully opened position;
   the distal end of each jaw tip including a recess, a first portion of which undercuts said base, the base and the edge of the recess forming an acute angle to form a stop for preventing a clip from receding from the tip of said jaws while it is being closed about a vessel to be ligated;
   each of said jaw tips including a planar exit portion stepped down below the plane of said channel base and extending from the distal end of said recess to the distal end of said jaw tip; and,
   the inwardly facing upper portion of each side wall of each channel having a convex curved portion extending axially along said channel from a point rearward of said recess to the end of each jaw tip to facilitate proper closure of a ligating clip despite misalignment of said jaw tips.

* * * * *

UNITED STATES PATENT AND TRADEMARK OFFICE
CERTIFICATE OF CORRECTION

PATENT NO. : 4,480,641

DATED : November 6, 1984

INVENTOR(S) : Stephen J. Failla, et al

It is certified that error appears in the above-identified patent and that said Letters Patent is hereby corrected as shown below:

Claims 1 and 3 should read as follows:

1. [Jaw tips for a] A medical instrument for applying a plurality of ligating clips, said instrument having jaw tips comprising:

a ligating clip having projecting portions;

a right and left jaw disposed in confronting relationship and adapted to move together to close a clip about a vessel to be ligated, each of said jaws including:

a generally U-shaped channel having a first and second side wall and a base, the base of each jaw tapering toward the other as one advances in a direction toward the jaw tips from the body of said instrument when said jaws are in the fully opened position to partially close [a] said clip as it is delivered to the jaw tips to assist in maintaining [the] said clip within said Ushaped channels;

UNITED STATES PATENT AND TRADEMARK OFFICE
CERTIFICATE OF CORRECTION

PATENT NO. : 4,480,641        Page 2 of 5
DATED     : November 6, 1984
INVENTOR(S) : Stephen J. Failla, et al It is certified that error appears in the above-identified patent and that said Letters Patent is hereby corrected as shown below:

the distal end of each jaw tip including a recess for receiving a projecting portion of said clip and for retaining said clip projection therein during closing, thereby preventing said clip from receding into said U-shaped channels as it is closed about a vessel;

said recess including a first portion which undercuts the base of each said U-shaped channel, the base and the edge of the recess forming an acute angle to provide a stop for preventing the clip from receding from the jaws while it is being closed about a vessel to be ligated, the bottom of said recess extending longitudinally of its jaw a distance greater than the projecting portion of said clip to facilitate the entry of the projecting portion on said clip into said recess;

UNITED STATES PATENT AND TRADEMARK OFFICE
CERTIFICATE OF CORRECTION

PATENT NO. : 4,480,641          Page 3 of 5
DATED : November 6, 1984
INVENTOR(S) : Stephen J. Failla, et al It is certified that error appears in the above-identified patent and that said Letters Patent is hereby corrected as shown below:

each said jaw tip further includes a planar exit portion stepped down below the plane of said U-shaped channel bases and extending from the distal end of each said recess to the distal end of each said jaw tip;

the inwardly facing, upper portion of each side wall of each said U-shaped channel includes a convex, curved portion extending longitudinally along said U-shaped channel from a point rearward of said recess to the end of each jaw tip to facilitate proper closure of the ligating clip despite misalignment of said jaw tips.

3. [Jaw tips for a] A medical instrument for applying a plurality of ligating clips, said instrument having jaw tips comprising:

UNITED STATES PATENT AND TRADEMARK OFFICE
CERTIFICATE OF CORRECTION

PATENT NO. : 4,480,641

DATED : November 6, 1984

INVENTOR(S) : Stephen J. Failla, et al

It is certified that error appears in the above-identified patent and that said Letters Patent is hereby corrected as shown below:

<u>a ligating clip having projecting portions;</u> a generally U-shaped channel having a first and second side wall and a base, the base of each jaw tip tapering toward one another as one advances in a direction toward the jaw tips from the body of said instrument when said jaws are in the fully opened position;

the distal end of each jaw tip including a recess, a first portion of which undercuts said base, the base and the edge of the recess forming an acute angle to form a stop for preventing [a] <u>said</u> clip from receding from the tip of said jaws [while] <u>as</u> it is [being] closed about a vessel to be ligated;

each of said jaw tips including a planar exit portion stepped down below the plane of said channel base and extending from the distal end of said recess to the distal end of said jaw tip; and,

UNITED STATES PATENT AND TRADEMARK OFFICE
CERTIFICATE OF CORRECTION

PATENT NO. : 4,480,641

DATED : November 6, 1984

INVENTOR(S) : Stephen J. Failla, et al

It is certified that error appears in the above-identified patent and that said Letters Patent is hereby corrected as shown below:

the inwardly facing upper portion of each side wall of each channel having a convex curved portion extending axially along said channel from a point rearward of said recess to the end of each jaw tip to facilitate proper closure of [a] said ligating clip despite misalignment of said jaw tips.

Signed and Sealed this

Nineteenth Day of November 1985

[SEAL]

Attest:

DONALD J. QUIGG

Attesting Officer     Commissioner of Patents and Trademarks